United States Patent

Yokomizo et al.

Patent Number: 4,464,647
Date of Patent: Aug. 7, 1984

[54] HUMIDITY SENSOR MADE OF METAL OXIDE

[75] Inventors: Yuji Yokomizo, Nagai; Keiji Yuuki, Takahata; Naoe Watanabe, Nagai, all of Japan

[73] Assignees: Marcon Electronics Co. Ltd., Nagai; Japan Electronic Industry Development Association, Mianto, both of Japan

[21] Appl. No.: 342,225

[22] Filed: Jan. 25, 1982

[30] Foreign Application Priority Data

Feb. 12, 1981 [JP] Japan .................................. 56-19758
May 8, 1981 [JP] Japan .................................. 56-69584
May 8, 1981 [JP] Japan .................................. 56-69585

[51] Int. Cl.$^3$ .............................................. H01B 1/00
[52] U.S. Cl. ........................................ 338/35; 73/336; 73/336.5; 252/517; 252/518; 252/519; 252/520; 252/521
[58] Field of Search ................. 338/35; 252/517, 518, 252/519, 520, 521; 73/336, 336.5; 324/65 R

[56] References Cited

U.S. PATENT DOCUMENTS 3,926,858 12/1975 Iuchinose et al. ................. 252/517
4,015,230 3/1977 Nitta et al. ............................. 338/35
4,080,564 3/1978 Nitta et al. ........................ 324/65 R

FOREIGN PATENT DOCUMENTS 7515014 6/1976 Netherlands ...................... 324/65 R Primary Examiner—Roy N. Envall, Jr.
Assistant Examiner—Christopher N. Sears
Attorney, Agent, or Firm—Oblon, Fisher, Spivak, McClelland & Maier

[57] ABSTRACT

A sintered body for a humidity sensor is formed by baking a blend at 1,000° to 1,400° C., the blend comprising ZnO, $Cr_2O_3$, $V_2O_5$ and $M_2O$ where $M_2O$ is at least one metal oxide selected from $Li_2O$, $Na_2O$ and $K_2O$. A pair of electrodes are each attached to the corresponding surface of the sintered body to obtain a humidity sensor of metal oxide which is relatively low in its resistive value and stable in its aging characteristic.

7 Claims, 14 Drawing Figures

F I G. 1
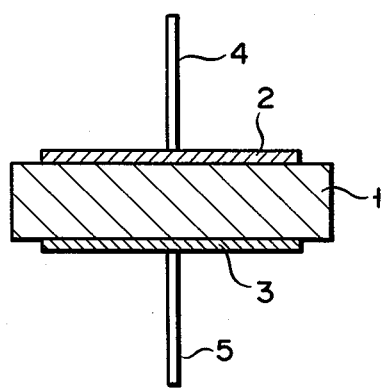
F I G. 2
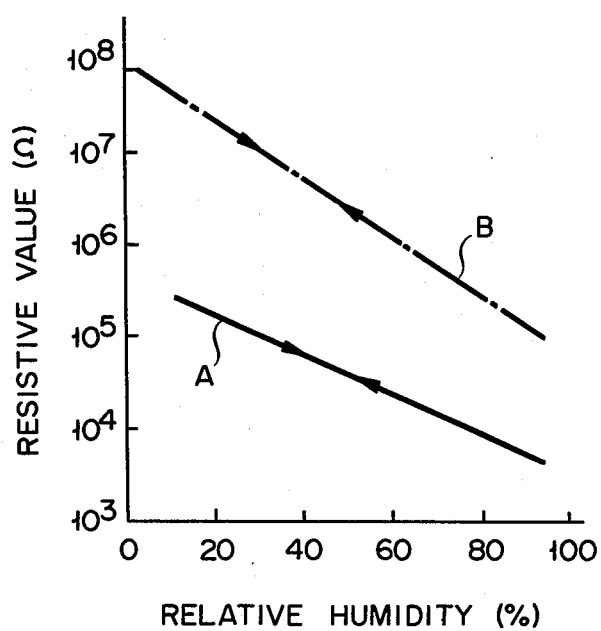

F I G. 11
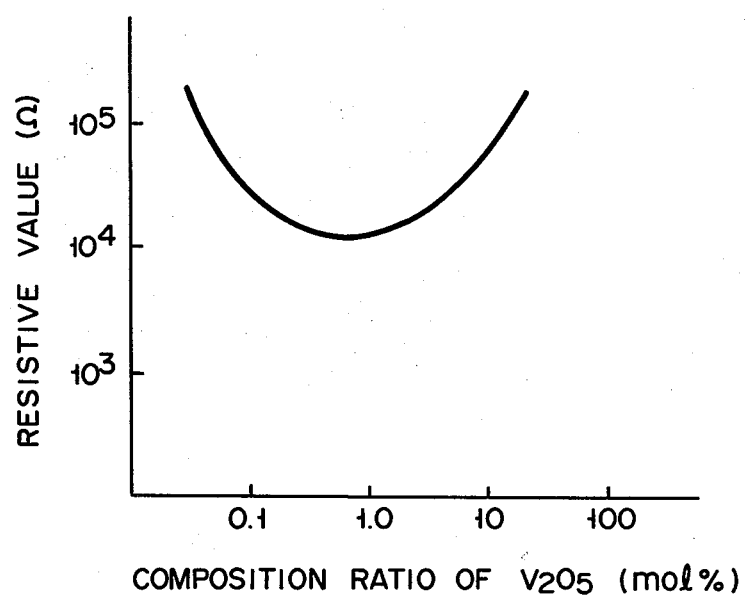
F I G. 12
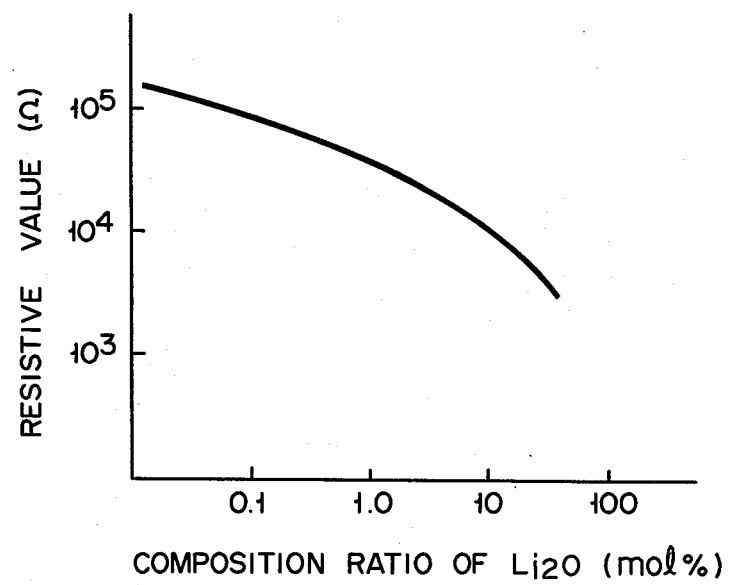

F I G. 13
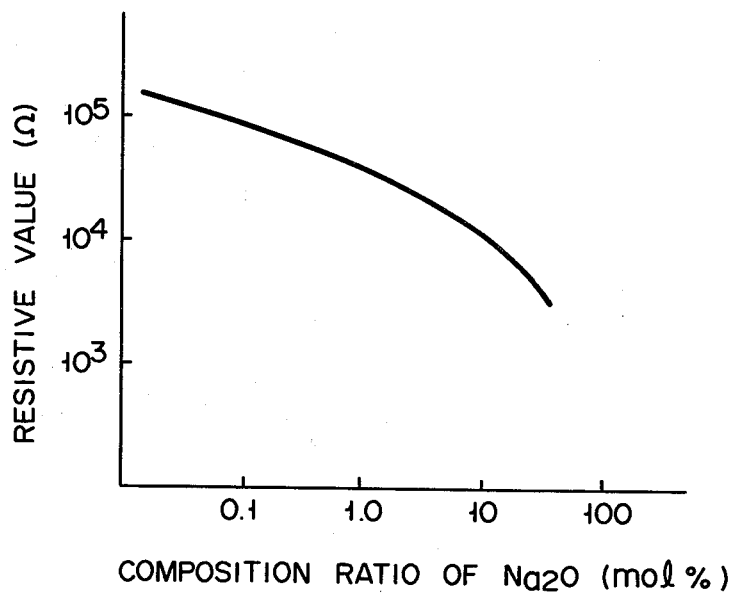
F I G. 14
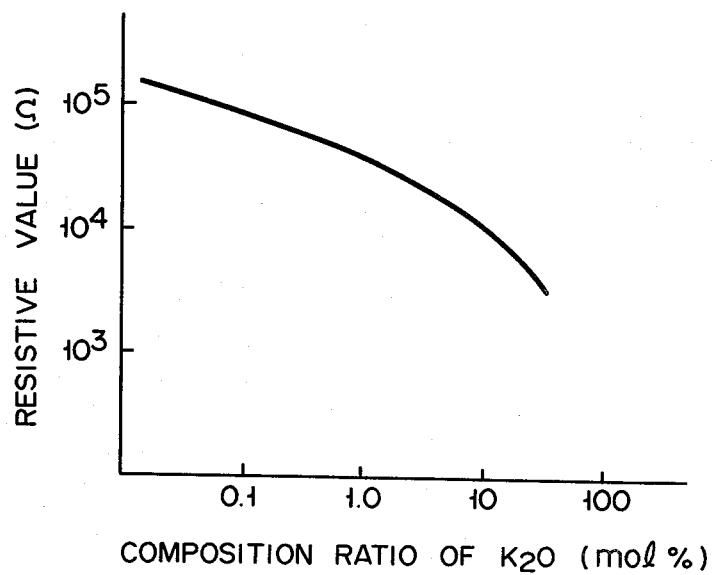

HUMIDITY SENSOR MADE OF METAL OXIDE

BACKGROUND OF THE INVENTION

This invention relates to a humidity sensor made of metal oxide and adapted to detect a change in humidity as a change of an electrical resistance.

Generally, metal oxide has excellent water-absorbing and water-removing properties, and an electrical resistance element made of metal oxide has such a property that its resistive value varies due to a change in humidity. It is known to use the electrical resistance element as a humidity element by utilizing such property.

In a conventional humidity sensor made of metal oxide such as $Fe_2O_3$, $Fe_3O_4$, $Al_2O_3$ and $Cr_2O_3$, the powder of metal oxide is coated onto the surfaces of an inorganic insulating substrate to form a humidity sensing film. The sensor utilizes such a phenomenon that the electrical resistive value of the humidity sensing film varies due to a variation in humidity. The humidity sensor made of metal oxide has physically, chemically and thermally stable properties, but has a relatively high resistivity. Since a rate of change of a resistance resulting from a change in humidity is relatively small, it is difficult to detect a change of an electrical resistance with high accuracy. Thus, it is impossible to effect a humidity detection with high accuracy.

A humidity sensor is also known which utilizes the semiconducting property of an oxide having, for example, a spinel structure. The sensor has a relatively low resistive value and permits a detection to be made over a whole relative humidity range of 0 to 100%. However, if the sensor is left at room temperature, there is a tendency that its resistive value will be increased, failing to obtain a reproducible humidity sensor. In order to improve the reproducibility of the humidity sensor an attempt is made to heat the humidity sensor. However, the aging characteristic of electrode material of the sensor will be deteriorated by repetitive heating, resulting in a poor reliability and moreover, a complicated structure is necessary. Further, since a rate of change of a resistive value to a change of humidity becomes markedly greater, no better matching is obtained in connecting the sensor to a measuring circuit.

SUMMARY OF THE INVENTION

It is accordingly an object of this invention to provide a humidity sensor made of metal oxide which is relatively low in its resistive value and relatively great in a rate of change of its resistive value to a change of humidity.

Another object of this invention is to provide a humidity sensor made of metal oxide which is relatively low in its resistive value and has such an aging property as to be stable in its resistive value even after it is left at room temperature in an air atmosphere for a long time.

Another object of this invention is to provide a humidity sensor made of metal oxide which is relatively low in its resistive value and smaller in its humidity hysteresis.

Another object of this invention is to provide a humidity sensor made of metal oxide which is relatively low in its resistive value and has a stable resistive value even after it is left at a high temperature of 85° C.

According to this invention there is provided a humidity sensor made of metal oxide comprising a sintered body made of a composition of 69.95 to 30 mol % of ZnO, 29.95 to 50 mol % of $Cr_2O_3$, 0.05 to 10 mol % of $V_2O_5$ and 0.05 to 10 mol % of $M_2O$ where $M_2O$ is at least one metal oxide selected from the group consisting of $Li_2O$, $Na_2O$ and $K_2O$; and a pair of electrodes each attached to the corresponding surface of said sintered body.

In another aspect of this invention there is provided a humidity sensor made of metal oxide which is obtained by prebaking a blend of a composition of 69.95 to 30 mol % of ZnO, 29.95 to 50 mol % of $Cr_2O_3$, 0.05 to 10 mol % of $V_2O_5$ and 0.05 to 10 mol % of $M_2O$ (where $M_2O$ is at least one metal oxide selected from $Li_2O$, $Na_2O$ and $K_2O$) and crushing the prebaked mass to powder, blending the powder with a binder and shaping the blend into a shaped mass under a pressure of 100 kg/cm2 to 1.2 ton/cm$^2$, sintering the shaped mass at a temperature of 1,000° C. to 1,400° C. for 1 to 5 hours to form a sintered body, and attaching each of a pair of electrodes to the corresponding surface of the sintered body.

BRIEF DESCRIPTION OF THE DRAWINGS

FIG. 1 is a cross-sectional view showing a humidity element according to one embodiment of this invention;

FIG. 2 is a characteristic curve showing a relation of a relative humidity to a resistive value;

FIG. 11 is a curve showing a relation of the composition ratio of $V_2O_5$ to its resistive value;

FIG. 12 is a curve showing a relation of the composition ratio of $Li_2O$ to its resistive value;

FIG. 13 is a curve showing a relation of the composition ratio of $Na_2O$ to its resistive value; and FIG. 14 is a curve showing a relation of the composition ratio of $K_2O$ to its resistive value.

DETAILED DESCRIPTION OF THE PREFERRED EMBODIMENTS

Figure 3:
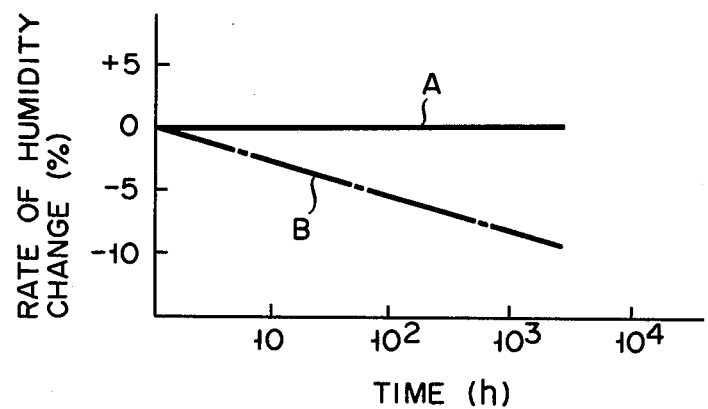
FIGS. 3 to 8, each, are an aging characteristic curve showing a time-to-humidity relation.

This invention will be explained below by referring to the accompanying drawings.

In FIG. 1, reference numeral 1 shows a sintered body 1 having a composition of 69.5 to 30 mol % of ZnO, 29.95 to 50 mol % of $Cr_2O_3$, 0.05 to 10 mol % of $V_2O_5$, and 0.05 to 10 mol % of $M_2O$ which is at least one metal oxide selected from $Li_2O$, $Na_2O$ and $K_2O$. The sintered body 1 corresponds to a humidity sensing section of the humidity sensor according to this invention. A pair of corrosion-resisting electrode materials having a good adhesion to the surface of the sintered body 1 are each bonded to the corresponding surface of the sintered body 1 to provide a pair of electrodes 2, 3. The electrode material is lower in its contact resistance and made of a metal paste such as gold and platinum, or an oxide paste such as ruthenium oxide and indium oxide. External terminals 4 and 5 for connection to, for example, a measuring circuit are each attached to the corresponding surface of the electrodes 2 and 3.

EXAMPLE (1)

47.5 mol % of ZnO, 42.5 mol % of $Cr_2O_3$, 5 mol % of $V_2O_5$ and 5 mol % of $Li_2O$ were weighed out and thoroughly blended, for example, on a ball mill. The blend was prebaked at a temperature of 850° C. for two hours and further crushed by, for example, the ball mill to powder. A binder such as polyvinyl alcohol was blended with the powder and the blend was shaped under a pressure of about 100 kg/cm² to 1.2 ton/cm² to a desired dimension. The shaped body was sintered at a temperature of 1,000° to 1,400° C. in an air atmosphere for 1 to 5 hours. A gold paste or a ruthenium paste was coated and baked to the respective surface of the resultant sintered body to provide a pair of electrodes 2, 3. A pair of terminals 4, 5 were each connected to the corresponding electrode (2, 3) to obtain a humidity sensor as shown in FIG. 1.

FIGS. 2 to 5 shows a comparison between the humidity sensor (A) of this invention and a humidity sensor (B) of a control in respect of their humidity-resistance characteristic, their aging characteristic and their hysteresis. The humidity sensor (B) of the control is an $MgCr_2O_4$ type humidity sensor which is made of an oxide of a spinel structure. A comparison of these sensors reveals that the sensor of this invention shows an excellent result. As evident from the humidity resistance characteristic of FIG. 2, the sensor (B) of the control has the disadvantages of being higher in its resistive value and about three orders of magnitude greater in its rate of change. Since the sensor (A) of this invention is lower in its resistive value and about two orders of magnitude greater in its rate of change, it can obtain a ready matching to the measuring circuit in comparison with the sensor (B).

Figure 4:
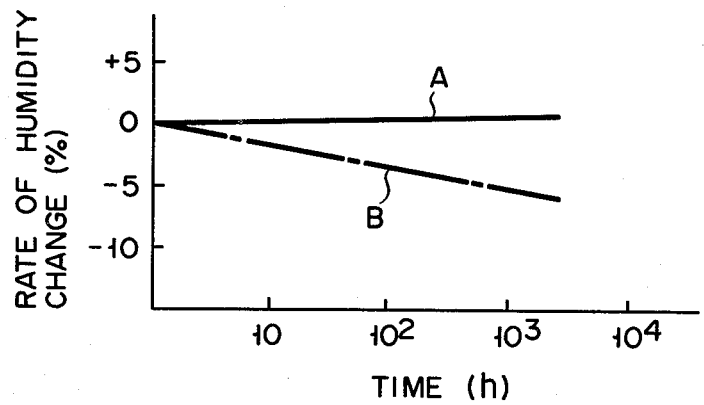
Figure 5:
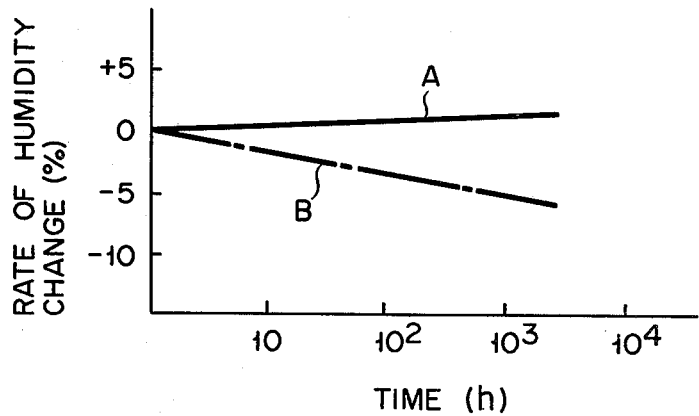

FIGS. 3 to 5 each show a comparison between the sensor (A) and the sensor (B) in respect to of its aging characteristic. The respective sensors were left at 35° C. in a relative humidity atmosphere of 90% for 1,000 hours and then the respective sensors at 25° C. in a relative humidity atmosphere of 50%, 70% and 90% were measured in their resistive values and compared with their initial values. A difference between the resistive value and their initial value was converted to a humidity variation and shown as a rate of humidity change FIGS. 3 to 5. FIGS. 3, 4 and 5 correspond to the relative humidities of 50%, 70% and 90%, respectively. From these Figures it will be appreciated that the rate of humidity change of the sensor (A) of this invention is stable with little change and that the rate of humidity change of the sensor of the control is greater in a minus direction.

Figure 6:
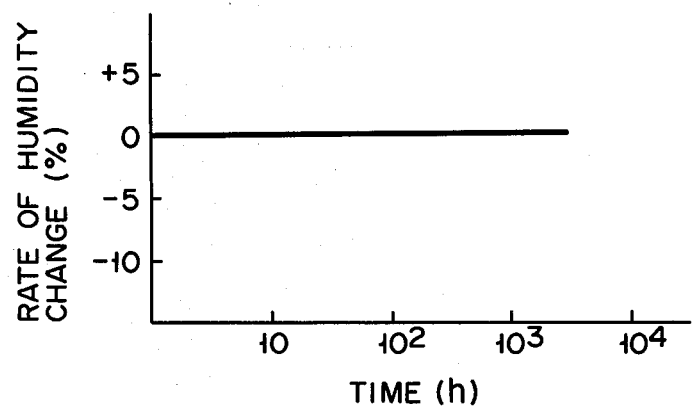
Figure 7:
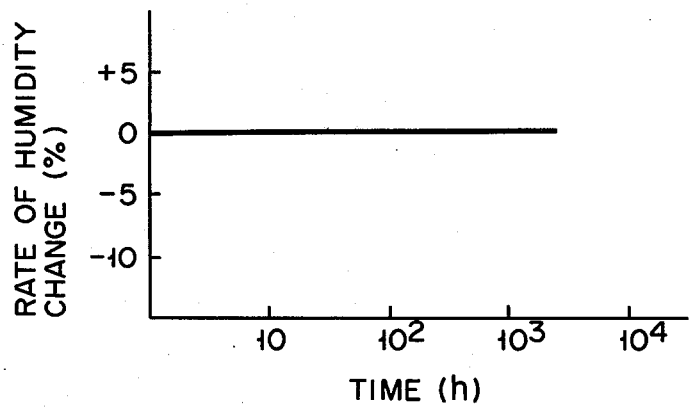
Figure 8:
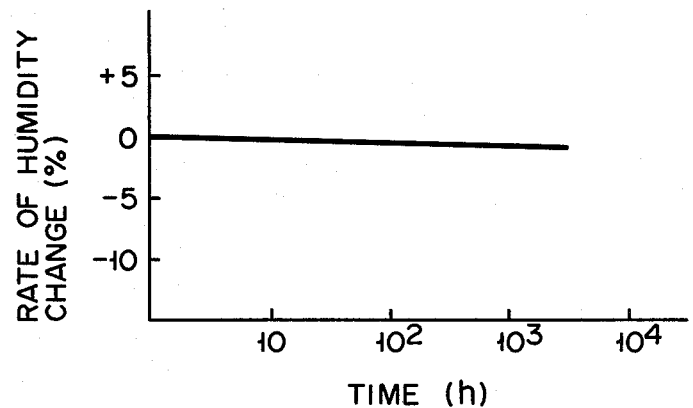

FIGS. 6 to 8 each show the aging characteristic at 85° C. of the sensor of this invention. The humidity sensor was left at 85° C. for 1,000 hours and the sensors at 25° C. in a relative humidity atmosphere of 50%, 70% and 90% were measured in their resistive values and compared with their initial values. A difference between the resistive value and their initial value were converted to a humidity variation and shown as a rate of humidity change. As evident from these Figures, the humidity sensor of this invention is stable in a high temperature atmosphere and can be satisfactorily used even at high temperature.

The reason why the respective composition ratio of ZnO, $Cr_2O_3$, $V_2O_5$ and $Li_2O$ are restricted as mentioned will be explained below in connection with FIGS. 9 to 12.

Figure 9:
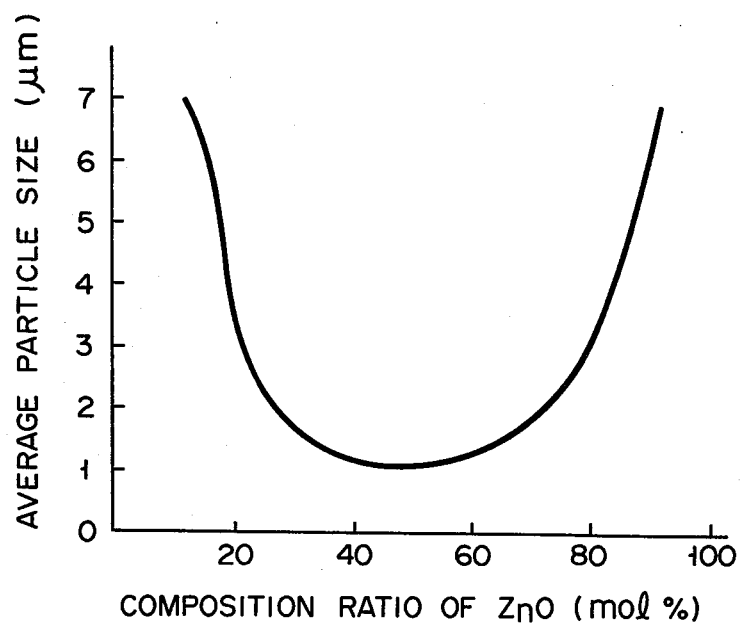
FIG. 9 is a graph showing a relation of the composition ratio of ZnO to its average particle size.

FIG. 9 shows a relation of the composition ratio of ZnO to the average particle size of the sintered body. As evident from FIG. 9, the average particle size of the sintered body exceeds 2 $\mu$m when ZnO is less than 30 mol % and in excess of 69.95 mol %. As a result, the sintered body is undesirable as a humidity sensor, because it has a smaller porosity.

Figure 10:
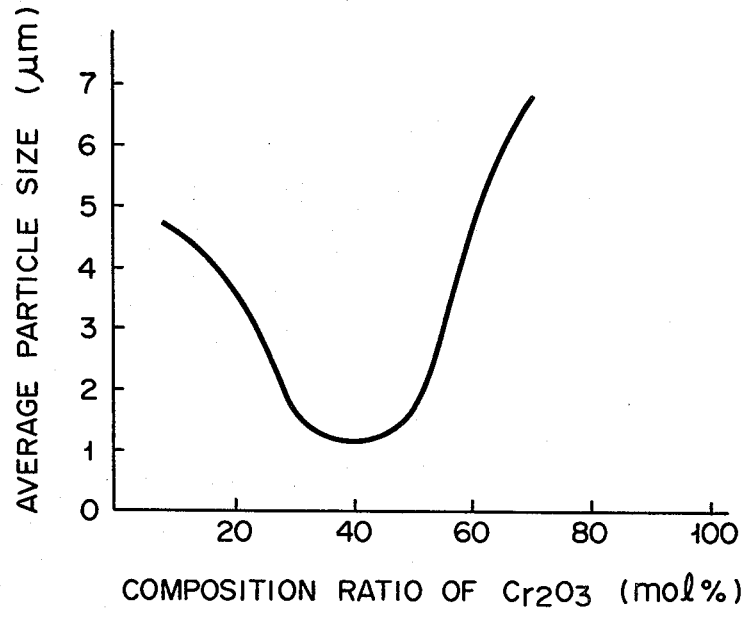
FIG. 10 is a graph showing a relation of the composition ratio of $Cr_2O_3$ to its average size.

FIG. 10 shows a relation of the composition ratio of $Cr_2O_3$ to the average particle size of the sintered body. Where $Cr_2O_3$ is less than 29.95 mol % and in excess of 50 mol %, the average particle size of the sintered body exceeds 2 $\mu$m as in the case of ZnO and is unsuitable as the humidity sensor, because the porosity of the sintered body becomes smaller.

FIG. 11 shows a relation of the composition ratio of $V_2O_5$ at a relative humidity of 60% to a resistive value. From FIG. 11 it will be appreciated that in a range of 0.05 to 10 mol % of $V_2O_5$ the resistive value enters into a range of $10^4$ $\Omega$, but that the resistive value is increased if $V_2O_5$ is less than 0.05 mol % and in excess of 10 mol %. This results in a poor matching between the humidity sensor and the measuring circuit and is unsuitable as the humidity sensor.

FIG. 12 is a graph showing a relation of a change of a resistive value to the composition ratio of $Li_2O$. From FIG. 12 it will be appreciated that for a range of 0.05 to 10 mol % of $Li_2O$ the resistive value enters into a range of $10^4$ $\Omega$, but that for less than 0.05 mol % of $Li_2O$ the resistive value is increased and a poor matching between the sensor and the measuring circuit results. If $Li_2O$ exceeds 10 mol %, a lowing in the resistive value and a poor aging characteristic results, and thus no good humidity sensor is obtained.

From the above explanations it will be understood that the best composition range is 69.95 to 30 mol % of ZnO, 29.95 to 50 mol % of $Cr_2O_3$, 0.05 to 10 mol % of $V_2O_5$ and 0.05 to 10 mol % of $Li_2O$.

EXAMPLE 2

47.5 mol % of ZnO, 42.5 mol % of $Cr_2O_3$, 5 mol % of $V_2O_5$ and 5 mol % of $Na_2O$ were blended and processed as in Example 1 to obtain a sintered body 1. A pair of electrodes 2, 3 were each formed on the corresponding surface of the sintered body and terminals 4 and 5 were connected to the electrodes 4 and 5, respectively, to provide a humidity sensor as shown in FIG. 1.

The characteristics of the humidity sensor so obtained have been found substantially identical to those of the humidity sensor of this invention as already mentioned, and further explanation is therefore omitted.

Example 2 of this invention is the same as Example 1 of this invention in respect of its composition ratio and the reasons for its numerical restriction, except that $Li_2O$ is replaced by $Na_2O$. Therefore, further explanation is omitted.

FIG. 13 is a characteristic curve showing a relation of a change of the resistive value to the composition ratio of $Na_2O$. This characteristic curve is substantially the same as the $Li_2O$ characteristic curve of Example 1 as shown in FIG. 12, and further explanation is therefore omitted.

EXAMPLE 3

47.5 mol % of ZnO, 42.5 mol % of $Cr_2O_3$, 5 mol % of $V_2O_5$ and 5 mol % of $K_2O$ were blended and processed as in Example 1 to obtain a sintered body 1. A pair of electrodes 2, 3 were each formed on the corresponding surface of the sintered body 1 and terminals 4 and 5 were connected to the electrodes 2 and 3, respectively, to obtain a humidity sensor as shown in FIG. 1.

The sensor so obtained had characteristics substantially indentical to those of the sensor of this invention and further explanation is therefore omitted.

This embodiment is identical to Example 1 in respect of its composition ratio as well as the reasons for its numerical restriction, except that $Li_2O$ of Example 1 is replaced by $K_2O$, and further explanation is therefore omitted.

FIG. 14 shows a characteristic curve showing a relation of a change of a resistive value to the composition ratio of $K_2O$. This characteristic curve is substantially similar to the $Li_2O$ characteristic curve of Example 1 as shown in FIG. 12, and further explanation is therefore omitted.

EXAMPLE 4

47.5 mol % of ZnO, 42.5 mol % of $Cr_2O_3$, 5 mol % of $V_2O_5$, 3 mol % of $Li_2O$ and 2 mol % of $K_2O$ were blended and processed as in Example 1 to obtain a sintered body 1. A pair of electrodes 2, 3 were each formed on the corresponding surface of the sintered body 1 as in Example 1 and terminals 4 and 5 were connected to the electrodes 2 and 3, respectively, to obtain a humidity sensor as shown in FIG. 1.

The humidity sensor of Example 4 has characteristics substantially identical to those of Example 1 and further explanation is therefore omitted.

Example 4 is identical to Example 1 in respect of its composition ratio, as well as reasons for its numerical restrication, except that $Li_2O$ of Example 1 is replaced by a mixture of $Li_2O$ and $K_2O$, and further explanation is therefore omitted. The characteristic curve showing a variation of a resistive value to the composition ratio of the mixture of $Li_2O$ and $K_2O$ is substantially the same as the $Li_2O$ characteristic curve of Example 1 as shown in FIG. 12.

What we claim is:

1. A metal oxide humidity sensor comprising:
   a sintered body having an average particle size less than 2 μm and comprising 69.95 to 30 mol % of ZnO, 29.95 to 50 mol % or $Cr_2O_3$, 0.05 to 10 mol % of $V_2O_5$ and 0.05 to 10 mol % of $M_2O$ where $M_2O$ is at least one metal oxide selected from the group consisting of $Li_2O$, $Na_2O$ and $K_2O$; and
   a pair of electrodes each electrode being attached to a surface of said sintered body.

2. A humidity sensor according to claim 1, in which said sintered body is formed by a sintering step following two steps of (1) prebaking a blend of said composition and crushing it to powder and (2) blending the powder with a binder and shaping the blend into a shaped mass.

3. A humidity sensor according to claim 2, in which said prebaking step is carried out by heating a blend of said composition at 850° C. over about 2 hours.

4. A humidity sensor according to claim 2, in which said shaping step is carried out by subjecting said blend including said binder to a pressure of 100 kg/cm² to 1.2 ton/cm².

5. A humidity sensor according to claim 2, in which said shaped mass is sintered at a temperature of 1,000° to 1,400° C. for 1 to 5 hours.

6. A humidity sensor according to claim 1, in which said pair of electrodes are formed by coating, and baking, a metal paste selected from a gold paste and platinum paste onto both the surfaces of said sintered body.

7. A humidity sensor according to claim 1, in which said pair of electrodes are formed by coating, and baking, an oxide paste selected from the group consisting of ruthenium oxide and indium oxide, to both surfaces of said sintered body.

* * * * *